US006656508B2

(12) United States Patent
Goldenberg et al.

(10) Patent No.: US 6,656,508 B2
(45) Date of Patent: *Dec. 2, 2003

(54) SUSTAINED-RELEASE ALGINATE GELS

(75) Inventors: Merrill Seymour Goldenberg, Thousand Oaks, CA (US); Alice C. Beekman, Thousand Oaks, CA (US)

(73) Assignee: Amgen Inc., Thousand Oaks, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/842,756

(22) Filed: Apr. 17, 1997

(65) Prior Publication Data

US 2002/0001619 A1 Jan. 3, 2002

(51) Int. Cl.[7] .............................. A61K 9/14; A61K 9/10; A61K 47/36; A61K 47/02

(52) U.S. Cl. ........................ 424/499; 424/489; 424/500; 424/501; 424/484; 424/485; 424/486; 424/488; 914/944; 914/779

(58) Field of Search ................................ 424/484, 485, 424/488; 514/944, 779

(56) References Cited

U.S. PATENT DOCUMENTS

| | | | |
|---|---|---|---|
| 2,507,193 A | 5/1950 | Buckwalter .................. | 167/65 |
| 2,741,573 A | 4/1956 | Kirchmeyer et al. .......... | 167/58 |
| 2,882,203 A | 4/1959 | Petersen et al. .............. | 167/75 |
| 3,676,557 A | 7/1972 | Lachman et al. ........... | 424/260 |
| 4,352,883 A | * 10/1982 | Lim | |
| 4,400,391 A | * 8/1983 | Connick, Jr. | |
| 4,690,682 A | 9/1987 | Lim .......................... | 604/891 |
| 4,695,463 A | 9/1987 | Yang et al. .................. | 424/440 |
| 4,744,933 A | 5/1988 | Rha et al. .................... | 264/4.3 |
| 4,789,516 A | 12/1988 | Lim ......................... | 264/4.32 |
| 4,789,550 A | 12/1988 | Hommel et al. ............ | 424/493 |
| 4,880,830 A | * 11/1989 | Rhodes | |
| 4,933,185 A | * 6/1990 | Wheatley et al. | |
| 5,175,093 A | * 12/1992 | Seifert | |
| 5,192,802 A | * 3/1993 | Rencher | |
| 5,451,411 A | * 9/1995 | Gombotz et al. | |
| 5,700,848 A | * 12/1997 | Soon-Shiong et al. | |

FOREIGN PATENT DOCUMENTS

| | | |
|---|---|---|
| EP | 531 611 | 3/1993 |
| EP | 633 020 | 1/1995 |
| GB | 1 388 580 | 3/1975 |
| WO | WO 90/08551 | 8/1990 |
| WO | WO 90/11757 | 10/1990 |
| WO | WO 94/25080 | 11/1994 |
| WO | WO 95/29664 | 11/1995 |
| WO | WO 96/00081 | 1/1996 |
| WO | WO 96/03116 | 2/1996 |
| WO | WO 96/22792 | 8/1996 |
| WO | WO 97/01331 | 1/1997 |
| WO | WO 97/26916 | 7/1997 |
| WO | WO 97/28824 | 8/1997 |

OTHER PUBLICATIONS

Iannuccelli et al. (1993) 'Effect of the loading method on the drug release from cross–linked carboxymethylcellulose beads', *Journal of Controlled Release* 23:13–20.
Aslani et al., (1996) "Effect of Gelation Conditions and Dissolution Media on the Release of Paracetamol from Alginate Gel Beads", *J. Microencapsulation* 13(5):601–614.
Aslani et al., (1996) "Studies on Diffusion in Alginate Gels. I. Effect of Cross–linking with Calcium or Zinc Ions on Diffusion of Acetaminophen", *J. Control. Release* 42:75–82.
Bergmann et al., (1984) "Plasma Clearance, Tissue Distribution and Catabolism of Cationized Albumins with Increasing Isoelectric Points in the Rat", *Clinical Science* 67:35–43.
Bucke, (1987) "Cell Immobilization in Calcium Alginate", *Methods in Enzymology* 135:175–189.
Buckwalter et al., (1948) "A New Absorption Delaying Vehicle for Penicillin", *J. Am. Pharm. Assoc.*, Scientific Ed. pp. 472–474.
Chien, (1981) "Long–Acting Parenteral Drug Formulations", *J. Parenteral Sci. and Tech.*, 35(3):106–139.
Cottrell et al., "Alginates", in *Handbook of Water–Soluble Gums and Resins*, Ch. 2 (McGraw Hill Book Co. NY, ed. Davidson 1980) pp. 2–10—2–35.
Downs et al., (1992) "Calcium Alginate Beads as a Slow–Release System for Delivering Angiogenic Molecules In Vivo and In Vitro", *J. Cell. Physiol.* 152:422–429.
Draget et al., (1989) "Alginate–based solid media for plant tissue culture", *Appl. Microbiol Biotechnol.* 31:79–83.
Edelman et al., (1991) "Controlled and Modulated Release of Basic Fibroblast Growth Factor", *Biomaterials* 12:619–626.
Gray et al., (1988) "Retention of Insulin in Alginate Gel Beads", *Biotechnol. and Bioeng.* 31 607–612.
Huguet et al., (1994) "Hemoglobin Encapsulation in Chitosan/Calcium Alginate Beads", *J. Appl. Polym. Sci* 51:1427–1432.
Huguet et al., (1996) "Calcium Alginate Beads Coated with Chitosan: Effect of the Structure of Encapsulated Materials on Their Release", *Process Biochem.* 31(8):745–751.
Hwang et al., "Encapsulation with Chitosan: Trans–Membrane Diffusion of Proteins in Capsules", in *Chitin in Nature and Technology* (Plenum Press, NY, eds. Muzzarelli et al. 1986) pp. 389–396.
Johnson et al., (1996) "A Month–Long Effect from a Single Injection of Microencapsulated Human Growth Hormone", *Nature Med.* 2(7):795–799.
Kelco Technical Bulletin TS–4, "Reversible Sequestrant Algin Gel System".

(List continued on next page.)

Primary Examiner—Edward J Webman
(74) Attorney, Agent, or Firm—Joan D. Eggert; Stuart L. Watt; Ron K. Levy

(57) ABSTRACT

The present invention relates to sustained-release formulations using alginate gel beads and methods thereof.

18 Claims, No Drawings-

OTHER PUBLICATIONS

Kelco Technical Bulletin DDP–1, "Kelco Products: Pharmaceutical and Personal Care Applications".

Kelco Technical Bulletin DB–2, "Self–Gelling Ammonium–Calcium Alginate".

Klein et al., "New Developments in the Preparation and Characterization of Polymerbound Biocatalysts", in *Enzyme Engineering*, vol. 6 (Plenum Press, NY, eds Chibata et al. 1982) pp. 181–189.

Liu et al., (1995) "The Potential Application of Alginate/Chitosan Porous Microsphere Loaded with Interleukin–2 in Tumour Immunotherapy", *Proceed. Intern. Symp. Control. Bioact. Mater.* 22: 542–543.

Liu et al. (1997) "Controlled Release of Interleukin–2 for Tumour Immunotherapy Using Alginate/Chitosan Porous Microspheres", *J. Control Rel.* 43:65–74.

Macek, (1963) "Preparation of Parenteral Dispersions", *J. Pharm. Sci* 52(7):694–699.

Maysinger et al., (1992) "Microencapsulated Nerve Growth Factor: Effects on the Forebrain Neurons Following Devascularizing Cortical Lesions", *Neurosci. Letters* 140:71–74.

McDowell, *Properties of Alginates* (Alginate Industries $2^{ND}$ Edition, 1961).

Mittal et al., (1994) "In Vitro Effects of Brain Derived Neurotrophic Factor Released from Microspheres", *Neuro Report* 5(18):2577–2582.

Mózes et al., (1966) "Generalized Newtonian Fluids and Structural Viscosity. Thixotrophic Phenomena", *Int'l. Chem. Eng.* 6(1):150–159.

Okhamafe et al., (1996) "Modulation of protein release from chitosan–alginate microcapsules using the pH–sensitive polymer hydroxypropyl methylcellulose acetate succinate", *J. Microencapsulation* 13(5) 497–508.

Padol et al., (1986) "Some Observations on the Formation and Properties of Alginate–Poly (L–lysine) Microcapsules", *Proc. CRS* pp. 216–217.

Polk et al., (1994) "Controlled Release of Albumin from Chitosan–Alginate Microcapsules", *J. Pharm. Sci.* 83(2):178–185.

Poncelet et al., (1995) "Production of alginate beads by emulsification/internal gelation. II. Physicochemistry", *Appl. Microbiol. Biotechnol.* 43:644–650.

Puolakkainen et al., (1994) "Novel Delivery System for Inducting Quiescence in Intestinal Stem Cells in Rats by Transforming Growth Factor β1", *Gastroenterology* 107(5):1319–1326.

Smidsrød et al., (1990) "Alginate as Immobilization Matrix for Cells", *Trends in Biotechnology* 8:71–78.

Tanaka et al., (1984) "Diffusion Characteristics of Substrates in Ca–Alginate Gel Beads", *Biotechnol. and Bioeng.* 26 53–58.

Thies "Gelation", *How to Make Microcapsules*, Ch 6 (Course Manual, Washington University, St. Louis, MO 1987) pp. 6.1–6.24.

Thompson, "Sustained Release of Parenteral Drugs", Paper presented at the Annual Meeting of the Parenteral Drug Association, New York, Oct. 16, 1959.

Thompson et al., (1959) "Studies on Long–acting Vitamin $B_{12}$ Preparation," *Am. J. Clin. Nutr.* 7:311–317.

Wee et al., (1995) "Evaluation of Alginate Microbeads for Intranasal Delivery of Ovalbumin", *Proc. Intern. Symp. Control. Bioact. Mater.* 22:566–567.

Wee et al., (1994) "Controlled Release of Recombinant Human Tumor Necrosis Factor Receptor From Alginate Beads", *Proc. Intern. Symp. Control. Bioact. Mater.* 21:730–731.

Wheatley et al., (1991) "Coated Alginate Microspheres: Factor Influencing the Controlled Delivery of Macromolecules", *J. Appl. Polym. Sci.* 43:2123–2135.

Zimmermann et al., (1992) "Production of Mitogen–Contamination Free Alginates with Variable Ratios of Mannuronic Acid to Guluronic Acid by Free Flow Electrophoresis", *Electrophoresis* 13:269–274.

\* cited by examiner

SUSTAINED-RELEASE ALGINATE GELS

FIELD OF THE INVENTION

The present invention relates to sustained-release formulations using alginate gel beads and methods thereof.

BACKGROUND

With the advances in genetic and cell engineering technologies, the availability of recombinant proteins has engendered advances in the use of proteins as medicaments for therapeutic applications. Many illnesses or conditions treated with pharmaceutical proteins require sustained protein levels to achieve the most effective therapeutic result. However, as with most protein pharmaceuticals, the generally short biological half-life requires frequent administration. These repeated injections are given at various intervals which result in fluctuating medication levels at a significant physical and monetary burden on the patients. Since many conditions respond better to controlled levels of a pharmaceutical, a need exists for controlled release of a medicament to provide longer periods of consistent release. Such sustained-release medicaments would provide the patient with not only enhanced prophylactic, therapeutic or diagnostic effects, but also a decrease in the frequency of injections as well as in overall costs.

Current attempts to sustain medication levels in humans or animals between doses have included the use of biodegradable polymers as matrices to control medicament release. For example, Great Britain Patent No. 1,388,580 discloses the use of hydrogels for sustained-release of insulin. U.S. Pat. No. 4,789,550 discloses the use of polylysine coated alginate microcapsules for delivery of protein by encapsulating living cells. Sustained-release attempts have also utilized anionic or cationic polymer compositions surrounded by ionic polymers of the opposite charge for encapsulating cells capable of producing biologically active compositions. U.S. Pat. No. 4,744,933. Likewise, multiple coats of anionic or cationic cross-linking polymers have also been disclosed as means for obtaining controlled release. U.S. Pat. Nos. 4,690,682 and 4,789,516. In addition, further attempts disclose the use of alginates alone, or alginates coated with other biodegradable polymers, for controlled release of polypeptide compositions or cation precipitates thereof. PCT WO 96/00081, PCT WO 95/29664 and PCT WO 96/03116.

These attempts, however, have provided insufficient means for obtaining sustained-release delivery of desired protein pharmaceuticals. It is generally known that the use of certain biodegradable polymers, e.g., polylactide co-glycolide, under in vivo conditions, exhibit high initial bursts of medicament release. Johnson, O. et al., Nature Med., 2/7: 795 (1996). Furthermore, it is generally known that proteins used with current forms of sustained-release preparations can undergo denaturation and lose their bioactivity upon exposure to the encapsulating agents. Such preparations use organic solvents which can have deleterious effects on the protein of choice. Finally, as discussed below, use of alginate alone has not provided the desired controlled protein release necessary for effective therapeutic results.

In general, alginates are well known, naturally occurring, anionic, polysaccharides comprised of 1,4-linked-β-D-mannuronic acid and α-L-guluronic acid. Smidsrod O. et al., Trends in Biotechnology, 8: 71–78 (1990); Aslani, P. et al., J. Microencapsulation, 13/5: 601–614 (1996). Alginates typically vary from 70% mannuronic acid and 30% guluronic acid, to 30% mannuronic acid and 70% guluronic acid. Smidsrod, supra. Alginic acid is water insoluble whereas salts formed with monovalent ions like sodium, potassium and ammonium are water soluble. McDowell, R. H., "Properties of Alginates" (London, Alginate Industries Ltd, 2nd edition 1961). Polyvalent cations are known to react with alginates and to spontaneously form gels.

Alginates have a wide variety of applications such as food additives, adhesives, pharmaceutical tablets and wound dressings. Alginates have also been recommended for protein separation techniques. For example, Gray, C. J. et al., in Biotechnology and Bioengineering, 31: 607–612 (1988) entrapped insulin in zinc/calcium alginate gels for separation of insulin from other serum proteins.

Alginate matrices have also been well documented for drug delivery systems, see for example U.S. Pat. No. 4,695,463 disclosing an alginate based chewing gum delivery system and pharmaceutical preparations. Alginate beads have been used for controlled release of various proteins such as: tumor necrosis factor receptor in cation-alginate beads coated with polycations, Wee, S. F, Proceed. Intern. Symp. Control. Rel. Bioact. Mater., 21: 730–31 (1994); transforming growth factor encapsulated in alginate beads, Puolakkainen, P. A. et al., Gastroenterology, 107: 1319–1326 (1994); angiogenic factors entrapped in calcium-alginate beads, Downs, E. C. et al., J. of Cellular Physiology, 152: 422–429 (1992); albumin entrapped in chitosan-alginate microcapsules, Polk, A. et al., J. Pharmaceutical Sciences, 83/2: 178–185 (1994) or chitosan-calcium alginate beads coated with polymers, Okhamafe, A. O. et al., J. Microencapsulation, 13/5: 497–508 (1996); hemoglobulin encapsulated with chitosan-calcium alginate beads, Huguet, M. L. et al., J. Applied Polymer Science, 51: 1427–1432 (1994), Huguet, M. L. et al., Process Biochemistry, 31: 745–751 (1996); and interleukin-2 encapsulated in alginat-echitosan microspheres, Liu, L. S. et al., Proceed. Intern. Symp. Control. Rel. Bioact. Mater, 22: 542–543 (1995).

Systems using alginate gel beads, or alginate/calcium gel beads, to entrap proteins suffer from lack of any sustained-release effect due to rapid release of the protein from the alginate beads. Liu, L. et al., J. Control. Rel., 43: 65–74 (1997). To avoid such rapid release, a number of the above systems attempt to use polycation polymer coatings (e.g., polylysine, chitosan) to retard the release of the protein alginate beads. See, e.g., Wheatley, M. A. et al., J. Applied Polymer Science, 43: 2123–2135 (1991); Wee, S. F. et al. supra; Liu, L. S. et al. supra; Wee, S. F. et al., Controlled Release Society, 22: 566–567 (1995) and Lim, et al. supra.

Polycations, such as polylysine, are positively charged polyelectrolytes which interact with the negatively charged alginate molecules to form a polyelectrolyte complexes that act as diffusion barriers on the bead surface. Problems can occur with the use of polycations in that: (1) such formulations maybe cytotoxic due to the polycations (Huguet, M. L. et al., suDra; Zimmermann, Ulrich, Electrophoresis, 13: 269 (1992); Bergmann, P. et al., Clincial Science, 67: 35 (1984)); (2) polycations are prone to oxidation; (3) beads with polycation coatings tend not to be erodible and build up in the body; (4) such formulations are made via laborious coating procedures which include multiple coatings of the polycation polylysine (Padol, et al., Proceed. Intern. Symp. Control. Rel. Bioact. Mater, 2: 216 (1986) and (5) ionic interactions between the protein and the polycations can result in loss of protein activity or cause protein instability.

Accordingly, a need exists to develop pharmaceutical formulations which achieve a better means of sustained-release for clinical applications. Numerous recombinant or natural proteins could benefit from constant long term release and thereby provide more effective clinical results.

The present invention provides such advances. Pharmaceutical compositions of the present invention are capable of providing protein protection, decreased degradation and slow release with increased protein stability and potency. Also, pharmaceutical compositions of the present invention provide a simple, rapid and inexpensive means of controlled recombinant protein release for effective prophylactic, therapeutic or diagnostic results.

SUMMARY OF THE INVENTION

The present invention relates to sustained-release formulations using alginate gel beads or particles, and methods thereof. In particular, the formation of the sustained-release gels includes the co-precipitation of alginate gel beads with a biologically active agent. This approach provides an advantage of producing efficient and high loading of biologically active agent within the alginate gel for sustained-release delivery while achieving protein protection, decreased degradation, increased stability and potency of the agent to be delivered.

Accordingly, one aspect of the present invention provides a sustained-release composition, comprising a hydrophilic polymer; a biologically active agent; and at least one precipitating agent. During the formulation of the composition the biologically active agent is co-precipitated with the hydrophilic polymer. In addition, additional precipitating agents may also be added to the composition. As used herein, the term co-precipitation refers to the use of agent(s) for precipitation of the biologically active agent together with the hydrophilic polymer so as to form a matrix of the precipitated polymer and agent, e.g., formation of alginate gel beads would be via precipitation. Such precipitation can be simultaneous or within close proximity thereto. The precipitation of molecules and any related precipitating agents are well known to those skilled in the art.

Another aspect provides for methods to produce the sustained-release compositions of the present invention. It comprises the steps of dissolving a biologically active agent and a hydrophilic polymer with a solvent to form a first mixture; dissolving at least one precipitating agent in a solvent to form a second mixture; adding the biologically active agent and the hydrophilic polymer solution of the first mixture with the precipitating agent and solvent of the second mixture; and co-precipitating the biologically active agent within the hydrophilic polymer. The present methods can also include the use of additional precipitating agents. In addition, a step for isolating the sustained-release composition is also contemplated.

As used herein, the term solvent refers to aqueous based solvents capable of dispersing or dissolving the biologically active agents, hydrophilic polymers or precipitating agents of choice. Such solvents are well known to one skilled in the art. Addition of the first mixture with the second mixture to form the co-precipitation composition can be done by methods well known to one skilled in the art, including but not limited to droplet addition, dispersion, spraying or mixing by using spray jets, air jets, atomizing, and electric fields. The term dispersion for purposes of this invention can mean a liquid, solid or gaseous dispersions. As used herein, the term isolating, refers to the process for isolation of the sustained-release composition of the present invention. Such isolation and purification procedures are well known in the art.

In yet another aspect, the present invention provides for a sustained-release composition produced by the above methods. Further aspects include pharmaceutical formulations of the above compositions in a pharmaceutically acceptable carrier, or adjuvant.

In yet other aspects, the present invention provides for methods of treating indications with sustained-release compositions containing desired biologically active agents.

DETAILED DESCRIPTION OF THE INVENTION

Compositions

Hydrophilic polymers including alginates and derivatives thereof, can be obtained from various commercial, natural or synthetic sources well known in the art. As used herein, the term hydrophilic polymer refers to water soluble polymers or polymers having affinity for absorbing water. Hydrophilic polymers are well known to one skilled in the art. These include but are not limited to polyanions, including anionic polysaccharides such as alginate, carboxymethyl amylose, polyacrylic acid salts, polymethacrylic acid salts, ethylene maleic anhydride copolymer (half ester), carboxymethyl cellulose, dextran sulfate, heparin, carboxymethyl dextran, carboxy cellulose, 2,3-dicarboxycellulose, tricarboxycellulose, carboxy gum arabic, carboxy carrageenan, carboxy pectin, carboxy tragacanth gum, carboxy xanthan gum, pentosan polysulfate, carboxy starch, carboxymethyl chitin/chitosan, curdlan, inositol hexasulfate, β-cyclodextrin sulfate, hyaluronic acid, chondroitin-6-sulfate, dermatan sulfate, heparin sulfate, carboxymethyl starch, carrageenan, polygalacturonate, carboxy guar gum, polyphosphate, polyaldehydo-carbonic acid, poly-1-hydroxy-1-sulfonate-propen-2, copolystyrene maleic acid, agarose, mesoglycan, sulfopropylated polyvinyl alcohols, cellulose sulfate, protamine sulfate, phospho guar gum, polyglutamic acid, polyaspartic acid, polyamino acids, derivatives or combinations thereof. One skilled in the art will appreciate other various hydrophilic polymers that are within the scope of the present invention.

Likewise, precipitating agents can be obtained from various commercial, natural or synthetic sources which are well known in the art. Precipitating agents include but are not limited to polyvalent metal ions, salts, acetates, citrates, chlorides, carbonates, hydroxides, oxalates, tartrates or hydroxides thereof, acids or water soluble polymers. In particular, the metal ions can include but are not limited to aluminum, barium, calcium, iron, manganese magnesium, strontium and zinc. Preferably the metal ions are calcium and zinc or the salts thereof, like zinc acetate, calcium acetate or chloride salts. Water soluble small molecules and salts can also be used such as ammonium sulfate, acetone, ethanol and glycerol.

As for water soluble polymers these include but are not limited to polyethylene glycol, ethylene glycol/propylene glycol copolymers, carboxylmethylcellulose, dextran, polyvinyl alcohol, polyvinyl pyrolidone, poly-1, 3-dioxolane, poly-1,3,6-trioxane, ethylene/maleic anhydride copolymers, polyaminoacids, dextran, poly (n-vinyl pyrolidone) polyethylene glycol, propylene glycol homopolymers, polypropylene oxide/ethylene oxide copolymers, polyoxyethylated polyols, polyvinyl alcohol succinate, glycerine, ethylene oxides, propylene oxides, poloxamers, alkoxylated copolymers, water soluble polyanions, derivatives or combinations thereof. The water soluble polymer may be of any molecular weight, and may be branched or unbranched. For example, the preferred molecular weight of polyethylene glycol is between about 700 Da and about 100 kDa for ease in handling and efficiency of precipitation.

Other sizes and types of precipitating agents, may be used, depending on the desired therapeutic profile (e.g., the duration of sustained-release desired, the effects, if any on biological activity, the ease in handling, the degree or lack of antigenicity and other known effects of a desired precipitating agent to a therapeutic protein or analog). One skilled in the art will appreciate other precipitating agents that are within the scope of the invention.

As used herein, the term buffer or buffer solution refers to use of inorganic or organic acids or a combination thereof to prepare a buffer solution as known in the art. Inorganic acids within the scope of the present invention include hydrogen halide (e.g., hydrochloric acid), phosphoric, nitric or sulfuric. Other inorganic acids would be well known to one skilled in the art and are contemplated herein. Organic acids within the scope of the invention include aliphatic carboxylic acids and aromatic acids such as formic, carbonic, acetic, propionic, butyric, valeric, caproic, acrylic, malonic, succinic, glutaric, adipic, maleic, fumaric, glycine or phenol sulfonic. Other organic acids would be well known to one skilled in the art. The preferred buffer of the present invention includes glycine and glycine phosphoric acid buffer systems.

As used herein, biologically active agents refers to recombinant or naturally occurring proteins, whether human or animal, useful for prophylactic, therapeutic or diagnostic application. The biologically active agent can be natural, synthetic, semi-synthetic or derivatives thereof. The biologically active agents of the present invention must be precipitable. A wide range of biologically active agents are contemplated. These include but are not limited to hormones, cytokines, hematopoietic factors, growth factors, antiobesity factors, trophic factors, anti-inflammatory factors, and enzymes (see also U.S. Pat. No. 4,695,463 for additional examples of useful biologically active agents). One skilled in the art will readily be able to adapt a desired biologically active agent to the compositions of present invention.

Such proteins would include but are not limited to interferons (see, U.S. Pat. Nos. 5,372,808, 5,541,293 4,897,471, and 4,695,623 hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), granulocyte-colony stimulating factors (see, U.S. Pat. Nos. 4,810,643, 4,999,291, 5,581,476, 5,582, 823, and PCT Publication No. 94/17185, hereby incorporated by reference including drawings, stem cell factor (PCT Publication Nos. 91/05795, 92/17505 and 95/17206, hereby incorporated by reference including drawings), and the OB protein (see PCT publication Nos. 96/40912, 96/05309, 97/00128, 97/01010 and 97/06816 hereby incorporated by reference including figures). In addition, biologically active agents can also include but are not limited to anti-obesity related products, insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), interleukins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakeratinocyte derived growth factor (MGDF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase and kallikrein. The term proteins, as used herein, includes peptides, polypeptides, consensus molecules, analogs, derivatives or combinations thereof.

Derivatives of biologically active agents may included the attachment of one or more chemical moieties to the protein moiety. Chemical modification of biologically active agents has been found to provide additional advantages under certain circumstances, such as increasing the stability and circulation time of the therapeutic protein and decreasing immunogenicity. One skilled in the art will be able to select the desired chemical modification based on the desired dosage, circulation time, resistance to proteolysis, therapeutic uses and other considerations.

Complexes

The proteins, analog or derivative may be administered complexed to a binding composition. Such binding composition may have the effect of prolonging the circulation time of the protein, analog or derivative or enhancing the activity of the biologically active agent. Such composition may be a protein (or synonymously, peptide), derivative, analog or combination. For example, a binding protein for the OB protein is OB protein receptor or portion thereof, such as a soluble portion thereof. Other binding proteins may be ascertained by examining OB protein, or the protein of choice, in serum, or be empirically screening for the presence of binding. Such binding will typically not interfere with the ability of OB protein or analog or derivative to bind to endogenous OB protein receptor and/or effect signal transduction. In addition to the OB protein, binding complexes will also be applicable to other therapeutic proteins of the present invention as well. Those well skilled in the art will be able to ascertain appropriate binding proteins for use with the present invention.

Pharmaceutical Compositions

The sustained-release pharmaceutical compositions of the present invention may be administered by oral (e.g., capsules such as hard capsules and soft capsules, solid preparations such as granules, tablets, pills, troches or lozenges, cachets, pellets, powder and lyophized forms, liquid preparations such as suspensions) and non-oral preparations (e.g., intramuscular, subcutaneous, transdermal, visceral, IV (intravenous), IP (intraperitoneal), intraarterial, intrathecal, intracapsular, intraorbital, injectable, pulmonary, nasal, rectal, and uterine-transmucosal preparations). In general, comprehended by the invention are sustained-release pharmaceutical compositions comprising effective amounts of protein, or derivative products, with the sustained-release compositions of the invention together with pharmaceutically acceptable diluents, preservatives, solubilizers, emulsifiers, adjuvants and/or carriers needed for administration. See PCT 97/01331 hereby incorporated by reference. The optimal pharmaceutical formulation for a desired biogically active agent will be determined by one skilled in the art depending upon the route of administration and desired dosage. Exemplary pharmaceutical compositions are disclosed in Remington's Pharmaceutical Sciences (Mack Publishing Co., 18th Ed., Easton, Pa., pgs. 1435–1712 (1990)).

Components that may be needed for administration include diluents of various buffer content (e.g., Tris-HCl, acetate), pH and ionic strength; additives such as surfactants and solubilizing agents (e.g., Tween 80, HCO-60, Polysorbate 80), antioxidants (e.g., ascorbic acid, glutathione, sodium metabisulfite), additional polysaccharides (e.g., carboxymethylcellulose, sodium alginate, sodium hyaluronate, protamine sulfate, polyethylene glycol), preservatives (e.g., Thimersol, benzyl alcohol, methyl paraben, propyl paraben) and building substances (e.g., lactose, mannitol); incorporation of the material into particulate preparations of polymeric compounds such as polylactic/polyglycolic acid polymers or copolymers, etc. or combined with liposomes. Hylauronic acid may also be used as an administration component and this may have the effect of promoting even further the sustained duration in the circulation. Additionally, sustained-release compositions of the present invention may also be dispersed with oils (e.g., sesame oil, corn oil, vegetable), or a mixture thereof with a phospholipid (e.g., lecitin), or medium chain fatty acid triglycerides (e.g., Miglyol 812) to provide an oily suspension. The compositions of the present invention may also be dispersed with dispersing agents such as water-soluble polysaccharides (e.g., mannitol, lactose, glucose, starches), hyaluronic acid, glycine, fibrin, collagen and inorganic salts (e.g., sodium chloride).

In addition, also contemplated for use in the administration of the sustained-release compositions of the present invention are mechanical devices designed for pulmonary delivery of therapeutic products, including but not limited to nebulizers, metered dose inhalers, and powder inhalers, all of which are familiar to those skilled in the art.

The administration components may influence the physical state, stability, rate of in vivo release, and rate of in vivo clearance of the present proteins and derivatives. One skilled in the art will appreciate the appropriate administration components and/or the appropriate mechanical devices to use depending on the therapeutic use, route of administration, desired dosage, circulation time, resistance to proteolysis, protein stability and other considerations.

Methods of Use

Therapeutic. Therapeutic uses depend on the biologically active agent used. One skilled in the art will readily be able to adapt a desired biologically active agent to the present invention for its intended therapeutic uses. Therapeutic uses for such agents are set forth in greater detail in the following publications hereby incorporated by reference including drawings. Therapeutic uses include but are not limited to uses for proteins like interferons (see, U.S. Pat. Nos. 5,372,808, 5,541,293 4,897,471, and 4,695,623 hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), granulocyte-colony stimulating factors (see, U.S. Pat. Nos. 4,999,291, 5,581,476, 5,582,823, 4,810,643 and PCT Publication No. 94/17185, hereby incorporated by reference including drawings), stem cell factor (PCT Publication Nos. 91/05795, 92/17505 and 95/17206, hereby incorporated by reference including drawings), and the OB protein (see PCT publication Nos. 96/40912, 96/05309, 97/00128, 97/01010 and 97/06816 hereby incorporated by reference including figures).

In addition, therapeutic uses of the present invention include uses of biologically active agents including but not limited to anti-obesity related products, insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), interluekins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakeratinocyte derived growth factor (MGDF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase and kallikrein. The term proteins, as used herein, includes peptides, polypeptides, consensus molecules, analogs, derivatives or combinations thereof. In addition, the present compositions may also be used for manufacture of one or more medicaments for treatment or amelioration of the conditions the biologically active agent is intended to treat.

By way of example, therapeutic uses oxygenation in the blood) and a decrease in bone resorption or osteoporosis may also be achieved in the absence of weight loss.

Combination Therapies. The present compositions and methods may be used in conjunction with other therapies, such as altered diet and exercise. Other medicaments, such as those useful for the treatment of diabetes (e.g., insulin, and possibly amylin), cholesterol and blood pressure lowering medicaments (such as those which reduce blood lipid levels or other cardiovascular medicaments), activity increasing medicaments (e.g., amphetamines), diuretics (for liquid elimination), and appetite suppressants. Such administration may be simultaneous or may be in seriatim. In addition, the present methods may be used in conjunction with surgical procedures, such as cosmetic surgeries designed to alter the overall appearance of a body (e.g., liposuction or laser surgeries designed to reduce body mass, or implant surgeries designed to increase the appearance of body mass). The health benefits of cardiac surgeries, such as bypass surgeries or other surgeries designed to relieve a deleterious condition caused by blockage of blood vessels by fatty deposits, such as arterial plaque, may be increased with concomitant use of the present compositions and methods. Methods to eliminate gall stones, such as ultrasonic or laser methods, may also be used either prior to, during or after a course of the present therapeutic methods. Furthermore, the present methods may be used as an adjunct to surgeries or therapies for broken bones, damaged muscle, or other therapies which would be improved by an increase in lean tissue mass.

Dosages

One skilled in the art will be able to ascertain effective dosages by administration and observing the desired therapeutic effect. The dosage of the sustained-release preparation is the amount necessary to achieve the effective concentration of the biologically active agent in vivo, for a given period of time. The dosage and the preferred administration frequency of the sustained-release preparations varies with the type of the biologically active agent, the desired duration of the release, the target disease, desired administration frequency, the subject animal species and other factors. Preferable, the formulation of the molecule will be such that between about 0.10 ug/kg/day and 100 mg/kg/day will yield the desired therapeutic effect.

The effective dosages may be determined using diagnostic tools over time. By way of example, the present invention provides the dosages of OB protein. For example, a diagnostic for measuring the amount of OB protein in the blood (or plasma or serum) may first be used to determine endogenous levels of OB protein. Such diagnostic tool may be in the form of an antibody assay, such as an antibody sandwich assay. The amount of endogenous OB protein is quantified initially, and a baseline is determined. The therapeutic dosages are determined as the quantification of endogenous and exogenous OB protein (that is, protein, analog or derivative found within the body, either self-produced or administered) is continued over the course of therapy. For example, a relatively high dosage may be needed initially, until therapeutic benefit is seen, and then lower dosages used to maintain the therapeutic benefits.

Methods of Preparation

Protein/Alginate Bead Preparation. A typical procedure is illustrated by the following example using the OB protein or leptin as the protein of choice. One skilled in the art will understand and be able to apply these procedures to other biologically active agents.

Preparation of the Drop Mixture. The term "drop mixture" as used herein refers to the mixture containing the hydrophilic polymer and the biologically active agent. A one mL mixture of 5% alginate (10 mM TRIS; pH 8) is added with magnetic stirring to 4 mL Leptin (100 mg/mL; 10 mM TRIS; pH 8) in a 10 mL beaker (in an ice bath). The mixture becomes cloudy. Then 40 mcL of 4 mM NaOH is added to the mixture and stirring is continued for 15 minutes (on ice). The mixture clarifies and its final pH is between approximately 8.6 to 8.8. The alginate concentration should at least be 0.05% by weight. In addition, the alginate should preferably be at least 30% guluronic acid.

In addition to the above, polyethylene glycol can be added to the drop mixture as discussed below. Likewise, buffers or excipients are helpful with stability of the protein of choice. One skilled in the art will be well aware of the appropriate ingredients that should be added for stability purposes depending on the protein chosen for delivery.

Preparation Of The Bath Mixture. The term "bath mixture" as used herein refers to the mixture which contains the precipitating agent(s) used for co-precipitation of the biologically active agent and the hydrophilic polymer. The bath typically contains 10 mL of mixture in a 50 mL beaker consisting of 100 mM CaCl2 plus other ingredients (see below). The pH is preferably acidic to help decrease the burst effect. The pH should be preferably less than pH 4. The buffer in the bath will also depend on the protein used. One skilled in the art will be able to adjust the buffer capacity or strength based on the protein used. Thus depending of the stability of the protein, if the buffer concentration is too high, for example with G-CSF, the protein may appear to be less stable and it will diminish the sustained-release.

The bath can be comprised of CaCl2, ZnCl2, polyethylene glycols ("PEG") and acidic buffers. The zinc interacts with the protein in precipitating it thereby helping to increase loading of the bead, decrease the burst effect and slow release of the protein from the bead. The calcium helps to form the alginate precipitate and formation of the bead. Calcium also helps to shape the bead, especially if the bath is viscous because of the addition of other additives like PEG. Calcium can be increased when you have increase viscosity to help maintain bead shape. Zinc concentrations should be at least 0.1 mM and calcium concentration should at least be 10 mM.

The addition of PEG helps to increase the loading. Certain PEGs are known to precipitate proteins. PEG can also be added to the protein/alginate mixture that is dropped into the bath to help maximize the loading and sustained-release. The molecular weight of PEG can range from 700 Da to 1000 kDa, but preferably 700 Da–100 kDa. One skilled in the art will be aware of the amount of PEG to add to the bath mixture but it can be as high as 99%, preferable less than 75% by weight. One skilled in the art will also be aware that the PEG concentration can be limited by viscosity of the bath.

Bead Preparation.

In general, droplets of a leptin/alginate drop mixture are sprayed, dripped or dispersed into a bath mixture (as described above) that precipitate or gels the leptin/alginate mixture. In addition, electrostatic means can be used for bead formation.

To make small beads, i.e. less than a few hundred microns in diameter, a flow chamber (nozzle holder) consisting of a needle with coaxial air flow is used. One of two ports is connected to a gas line and the other port to a syringe (3 mL) used to pump (at approximately 1 mL/min) the protein/alginate mixture into the bath. Typically 2 mL of the mixture is injected into 10 mL of bath mixture. The nozzle is positioned approximately 0.8 cm from the top of the bath beaker. The bead size is primarily determined by the gas flow rate, e.g., at a flow rate of 8 L/min the bead size ranges from 50–150 micron in diameter. The leptin/alginate flow rate has a much lesser effect on the bead size.

To make large (i.e., 1–3 mm diameter) beads, a 1 cc tuberculin syringe, fitted with a 24 G needle is used to drip the leptin/alginate mixture into the bath mixture. The bath typically contains 1.5% CaCl2 and 5 to 50 mM ZnCl2. The beads are collected by pouring them through a 40 micron nylon cell strainer. The beads are rinsed on the strainer with 5 mL sterile water and gently blotted from the underside of the strainer with a cleanroom wiper (gamma wipe 67). The beads are stored in a sterile plastic screw cap microtube.

Bead Loading

Burst Method: The drug loading of a selected group of beads is determined by accurately weighing 100 mg of the hydrated loaded beads into 1 mL of 0.5 M sodium citrate pH 8.5. The bead suspension is incubated at room temperature until the beads disintegrate usually forming a precipitate. The suspension is centrifuged at 14K rpm for 2 min. (eppendorf, 5415 C). The supernatant is collected and absorbance at 280 nm is recorded. The precipitate is dissolved by suspending it in 1 mL of 7 M urea. The absorbance of this mixture is recorded. The protein loading of the hydrated loaded beads is expressed as mg protein per mg bead or mg protein per mL bead and determined from the sum of the two absorbances.

Cumulative Method: This method is used in conjunction with the in vitro release studies. The amount of protein released from the beads including the burst at the end of the study is totalled. For details, see below.

In Vitro Release Studies

Hydrated loaded beads (100 mg) are weighed into a 1.5 mL microcentrifuge tube (eppendorf) and 1 mL buffer (10 mM histidine pH 7.4) added. The sample is placed in an incubator shaker at 37° C. and 100–200 rpm. At selected time intervals, the sample is removed from the incubator, centrifuged (eppendorf, 1000 rpm, 2 min) and the supernatant is removed and replaced with 1 mL of fresh buffer. The amount of protein released is determined from the absorbance of the supernatant. After the final released sample has been taken the amount left in the bead is determined by the Bead Loading/Burst Method. The percent released at a given time is determined from the summation of the total protein released and that remaining in the bead at the completion of the experiment.

In Vivo Studies

Mouse Weight Loss: In general, mice are injected once with a suspension of the loaded beads or unloaded beads. Six to eight week old female mice are used (type C57/BLC), typically weighing 20 grams. In the case of bead samples, 350 mcL of buffer (50 mM MES pH 6.7) is added to 100 mg of hydrated beads and vortexed. The suspension is drawn up into a 1 cc syringe and all the beads and 300 mcL of the buffer are injected (23 G needle) subcutaneously into the neck of the mouse. The mice are weighed daily.

Rat Pharmacokinetic Study: Six to eight week old female rats are used (type Sprague Dawley), typically weighing 250 grams. The injections are performed in a similar manner to that described in the mouse weight loss experiments. Blood is sampled by catheter collection at various time intervals post injection and the samples analyzed for leptin by an ELISA assay.

EXAMPLES

The following examples are offered to more fully illustrate the invention, but are not to be construed as limiting the scope thereof. In addition, with respects to the above disclosure or the examples below, one skilled in the art will be able to make the necessary changes to the disclosures for large scale production.

Example 1

This example examines the effect of leptin concentration in the bead on the release of leptin from zinc/leptin coprecipitated alginate beads. The small beads are prepared as described above using 25 mM ZnCl2 in the bath. The higher concentration bead, i.e. 66 mg/mL leptin, is prepared using 84 mg/mL leptin in 1% alginate while the lower concentration bead, i.e. 21 mg/mL leptin is prepared from 28 mg/mL leptin in 1% alginate. As the concentration of the leptin in the bead increases the fractional release of leptin from the bead decreases. For the higher concentration leptin 25% is released at 80 h, while at the lower concentration 80% is released at 80 h.

Example 2

This example examines the effect of bath ZnCl2 level on the release of leptin from zinc/leptin coprecipitated alginate beads. The small beads are prepared as described above but the ZnCl2 level in the bath is at 0.5 and 25 mM and the concentration of leptin in the beads is 37 mg/mL (by cumulative method). This example shows that as the ZnCl2 level in the bath increases the resultant beads have a decreased burst and decreased release rate of leptin. At 0.5 mM ZnCl2, the beads have a 20% burst and 50% release at 40 h; while at 25 mM ZnCl2 the beads have less than 5% burst and 25% release at 40 h.

Example 3

This example compares a zinc/leptin coprecipitate alginate bead with a control acetate buffer formulation(20 mg/mL) in a combined pharmacokinetic/bioactivity experiment. The small beads contain 64 mg/mL leptin (i.e., per mL of beads) and are fabricated as described above with 17 mM ZnCl2 in the bath. Female rats (220 g body weight) are given a single SC (subcutaneous) injection at 50 mg/kg dose. The plasma concentrations of the bead sample is sustained relative to that of the control. The rats injected with bead samples maintain a plasma concentration of leptin of over 50 ng/mL for over 112 h in contrast to that of 12–18 h for the control animals. The higher more sustained leptin blood levels in the bead group correlated with its more pronounced and sustained weight loss compared to the control group. The rats injected with bead samples continually lose weight for 120 h; at 120 h the total weight loss is 9% of the initial weight. In contrast, the control rats lose 7% of their initial weight in 50 h but regain the weight by 120 h.

Example 4

This example shows the effect of various PEGs in the bath, in addition to 10 mM ZnCl2, on the efficiency of loading and in vitro release of IL-1ra. The small beads are prepared as described above with IL-1ra in 10 mM PIPES pH 6.85. One bead bath (A) contains 100 mM CaCl2, 10 mM ZnCl2, 20% 1K PEG and 20% 2 K PEG. A second bead bath (B) contains the same as A but without 20% 1K PEG. The concentration of IL-1ra in beads A and B is 58 mg/mL, i.e. a loading efficiency of 74% as determined from the sodium citrate burst. The B formulation has a 55% burst and 75% released after 18 h. The A formulation has a 20% burst and 50% released after 18 h. Thus the addition of PEGs in the bath lead to highly loaded beads that sustain the release on the protein. Also, the addition of 1K PEK leads to an even lower burst and slower release of protein.

Example 5

This example shows the effect of having PEGs, but no zinc, in the bath on the loading of and initial burst of IL-1ra from alginate beads. The small beads are prepared as described above except the bath contains 20% 1K and 20% 2K PEG in addition to 100 mM CaCl2. The efficiency of loading is 93% with 63 mg/mL IL-1ra in the bead. The initial burst is 35%. Thus, the addition of PEGs to the bath can lead to high protein loading without the presence of zinc ions.

Example 6

In this example a comparison is made of effectiveness of the release of a bolus injection of IL-1ra in buffer (10 mM PIPES, pH 6.85) and IL-1ra in alginate beads of Example 1. Female Balb/C mice (20 g body weight) are injected SC (subcutaneously) at time zero with the various formulations each containing 10 mg of IL-1ra. At 18h the mice are injected IV (intravenously) with rhIL-1B (0.1 mcg per mouse) and then killed 2 h thereafter for blood sampling. Blood is analyzed for glucose concentration and lymphocyte numbers. IL-1beta normally causes a drop in glucose concentration and lymphocyte numbers but the presence of a certain level of IL-1ra protects against such a loss. The result of the experiment shows that only the mice that receive the IL-1ra contained in the beads are protected against the loss in value of the blood parameters. This results demonstrates that the alginate beads sustain the release of the IL-1ra at an effective level for at least 18 h.

Example 7

This example is a control experiment illustrating the preparation and release of protein containing beads using GCSF where the precipitation bath only contains CaCl2 (100 mM). The large beads are prepared as described above. The syringe mixture contains 46 mg/mL GCSF (10 mmM TRIS pH 7) in 1% alginate. The prepared beads contain 16 mg/mL GCSF (from citrate burst). Thus with only CaCl2 in the bath the efficiency of loading is 35%. The fractional release of the protein shows a 60% burst and 75% release in one day. Thus using a known procedure described in the literature one obtains low protein loading and rapid release.

Example 8

This example shows the effect of ZnCl2 in the bath on the loading and release of GCSF in alginate beads. The large beads are prepared as described above except 10 IM ZnCl2 is added to the bath. The syringe mixture contains 46 mg/mL GCSF in 1% alginate. The prepared beads contain 28 mg/mL GCSF (from citrate burst). Thus with the addition of 10 mM ZnCl2 to the bath (in addition to 100 mM CaCl2) the efficiency of loading increases from 35% (Example 6) to 61%. The fractional release of the protein shows a reduced burst of 40% and a one day release of 55%. Thus the addition of ZnCl2 to the CaCl2 bath leads to a higher loading efficiency, lower burst and slower release of protein.

Example 9

This example shows the effect of having PEG in the bath with the bath pH being acidic on the loading and release of GCSF with alginate beads. The large beads are prepared as described in Example 7 except 20% PEG (Aldrich) is added to the bath and the bath pH is 1.7. The bath also contains 100 mM CaCl2 and 10 mM ZnCl2. The loading efficiency for GCSF is 54% and the fractional release (25 mg/mL in the beads) shows a much reduced burst of less than 5% and 40% release after 100 hours. Thus an acidic bath mixture that can contain PEG (in addition to CaCl2 and ZnCl2) leads to low burst and slow release of protein.

Example 10

This example shows the effect of having PEGs and zinc in the bath and the bath pH lowered with acidifying agent(s) on the loading of and the initial burst of GCSF from alginate beads. The large beads are prepared as described above except the bath contains 25 mM ZnCl2, 100 mM CaCl2, and 5% PEG 1K and 5% PEG 10 K. The bath pH is lowered with glycine buffer and phosphoric acid to pH 1.65. The resultant beads (20 mg/mL loading) exhibit less than 5% burst and a fractional release of 40% in 90 h. Thus a combination of PEGs and zinc and low pH in the bath leads to a low burst and slow release.

Example 11

This example shows the preparation of GCSF in alginate beads with PEGs in a low pH bath without the addition of zinc ions. The small beads are prepared as described above except the bath contains 5% 1K and 5% 10K PEG. The bath pH is lowered to 1.43 using glycine and phosphoric acid buffer. The efficiency of loading is 42% with 14 mg/mL in the beads (from citrate burst). The fractional release shows a 32% burst and 35% release after 70 h.

Example 12

The large GCSF/alginate beads of Example 12, and Examples 13–15 below, are prepared in a similar manner to that described above but with more stringent control of the timing of the various operations and an alternate method to determine loading. More specifically, 1 mL of a GCSF/alginate mixture is dripped into 10 mL of the magnetically stirred bath in approximately 2 minutes. The beads are filtered and washed with 5 mL of water. The total bead making procedure takes approximately 5 minutes. The loading is determined (by A280) from the difference in the amount of protein in the alginate mixture dripped into the bath and the protein that does not get incorporated into the formed beads, i.e. the protein remaining in the bath mixture and the washes. This amount of protein incorporated into the beads is divided by the 1 mL volume of mixture added to the bath to obtain the loading expressed in mg/mL of beads.

Example 12 compares the presence of PEG in the bath on the loading of GCSF into the beads. The large beads are prepared as described above except the bath contains 200 mM CaCl2 and 15% PEG 8K (pH 5–6); the bath of the control beads has 200 mM CaCl2. The addition of PEG to the bath increases the loading from 21.8 mg/mL (70% efficiency) to 26.5 mg/mL (85% efficiency).

Example 13

This example shows the effect of low bath pH on the loading and release of GCSF with alginate beads. The bead formation and loading are determined as in Example 12 with PEG except one of the baths contains 0.5 M glycine buffer pH 2.1. The loading at pH 2.1, 24.9 mg/mL (80% efficiency), is similar to that of the control. However, the initial release at one hour (29%) is lower and the 24 h release more sustained (32%) than that of the control (92% and 99% respectively).

Example 14

This example shows the effect of the addition of zinc to a bath containing PEG on the loading of GCSF into alginate beads. The bead formation and loading are determined as in Example 12 with PEG. The addition of 10 mM ZnCl2 to the bath increased the loading from 26.5 mg/mL (85% efficiency) to 30.3 mg/mL (97% efficiency).

Example 15

This example shows a low initial burst and sustained-release of GCSF from alginate beads. The bead formation, loading and release are performed in a similar manner to that in EXAMPLE 13 except the bath contains 100 mM CaCl2, 5% PEG 1K and 5% PEG 2 K, and 0.5 M glycine buffer (pH 2.1). The loaded beads contain 24 mg/mL GCSF. At ½ h the initial release is near zero, at 19 h the release is 13.6% and at 44 h the release is 24%.

We claim:

1. A sustained-release gel bead composition for delivery by injection, comprising:
   a) a hydrophilic polymer;
   b) a biologically active agent; and
   c) at least two precipitating agents; wherein at least one of the precipitating agents is zinc and co-precipitates the biologically active agent, and further wherein the beads are formed in a mixture having an acidic pH.

2. The composition of claim 1 wherein at least one of the precipitating agents is selected from the group consisting of polyvalent metal ions, their corresponding salts, acetates, citrates, chlorides, carbonates, hydroxides and mixtures thereof.

3. The composition of claim 2 wherein the metal ions are selected from the group consisting of manganese, strontium, iron, magnesium, calcium, barium, aluminum and mixtures thereof.

4. The composition of claim 3 wherein the precipitating agents comprise calcium and zinc.

5. The composition of claim 1 wherein the hydrophilic polymer is a polyanion.

6. The composition of claim 1 wherein the hydrophilic polymer is a polysaccharide.

7. The composition of claim 6 wherein the polysaccharide is an acidic polysaccharide.

8. The composition of claim 7 wherein the polysaccharide is alginate.

9. The composition of claim 8 wherein the alginate contains at least 30% guluronic acid.

10. The composition of claim 8 wherein the alginate consist of at least 0.05% by weight.

11. The composition of claim 1 wherein the biologically active agent comprises a protein.

12. The composition of claim 11 wherein the protein consist of at least 0.01 mg/ml.

13. The composition of claim 11 wherein the protein is selected from the group consisting of hematopoetic factors, colony stimulating factors, anti-obesity factors, growth factors, trophic factors, and antiinflammatory factors.

14. The composition of claim 11 wherein the protein is selected from the group consisting of leptin, G-CSF, SCF, BDNF, GDNF, NT3, GM-CSF, IL-Ira, IL2, TNF-bp, MGDF, OPG, interferons, erythropoietin, KGF and analogs or derivatives thereof.

15. The composition of claim 1 wherein at least one of the precipitating agents is selected from the group consisting of water soluble polymers and mixtures thereof.

16. The composition of claim 15 wherein the water soluble polymer is polyethylene glycol.

17. A pharmaceutical formulation comprising a sustained-release composition according to claim 1 in a pharmaceutically acceptable carrier, diluent or adjuvant.

18. The composition of claim 1 or 4 wherein said mixture in which said beads are formed has a pH of less than pH 4.

* * * * *